United States Patent
Kraus et al.

(10) Patent No.: US 8,627,573 B2
(45) Date of Patent: Jan. 14, 2014

(54) HAIR-REMOVING DEVICE

(75) Inventors: Bernhard Kraus, Braunfels (DE); Alexander Klos, Hofheim (DE)

(73) Assignee: Braun GmbH, Kronberg (DE)

( * ) Notice: Subject to any disclaimer, the term of this patent is extended or adjusted under 35 U.S.C. 154(b) by 1746 days.

(21) Appl. No.: 11/099,018

(22) Filed: Apr. 5, 2005

(65) Prior Publication Data

US 2005/0216035 A1  Sep. 29, 2005

Related U.S. Application Data (63) Continuation of application No. PCT/EP03/10829, filed on Sep. 30, 2003.

(30) Foreign Application Priority Data

Oct. 5, 2002 (DE) .................................. 102 46 519

(51) Int. Cl.
*B26B 21/00* (2006.01)
*A61B 17/50* (2006.01)

(52) U.S. Cl.
USPC ............................................ 30/527; 606/133

(58) Field of Classification Search
USPC ........... 606/131, 133; 604/43; 30/34.05, 43.1, 30/43.4–43.92, 44, 45, 526, 527
See application file for complete search history.

(56) References Cited

U.S. PATENT DOCUMENTS

| | | | | |
|---|---|---|---|---|
| 3,093,900 A * | 6/1963 | Myers | ................................. | 30/45 |
| 4,575,902 A * | 3/1986 | Alazet | ................................. | 19/2 |
| 4,796,359 A | 1/1989 | Oprach et al. | | |
| 5,587,481 A * | 12/1996 | Allen et al. | .................... | 546/146 |
| 5,687,481 A | 11/1997 | De Boer et al. | | |
| 5,704,126 A * | 1/1998 | Franke et al. | .................. | 30/34.1 |
| 5,894,670 A * | 4/1999 | Iso et al. | .......................... | 30/541 |
| 5,983,502 A * | 11/1999 | Geertsma et al. | .............. | 30/43.6 |
| 6,009,623 A * | 1/2000 | Orloff | ............................. | 30/41.7 |
| 6,072,399 A * | 6/2000 | Cimbal et al. | ................ | 340/635 |
| 6,141,875 A * | 11/2000 | Andrews | ........................... | 30/50 |
| 6,261,301 B1 | 7/2001 | Knesch et al. | | |
| 2004/0098862 A1* | 5/2004 | Orloff | ............................. | 30/41.7 |
| 2004/0221947 A1* | 11/2004 | Haldner et al. | ............... | 156/250 |

FOREIGN PATENT DOCUMENTS

| | | |
|---|---|---|
| DE | 36 10 736 | 10/1987 |
| DE | 42 44 164 | 7/1993 |
| DE | 197 45 877 | 4/1999 |
| EP | 0 622 033 | 9/1998 |
| FR | 2 749 793 | 12/1997 |

* cited by examiner

*Primary Examiner* — Gary Jackson
*Assistant Examiner* — Lindsey Bachman
(74) *Attorney, Agent, or Firm* — Jerry J Yetter; Jason J Camp (57) ABSTRACT

The invention relates to a hair-removing device with a movable actuator head and/or at least one movable actuator support, which have at least one actuator element for removing hair on a skin surface. The particular feature of the invention is that a detecting device for detecting a parameter which relates to the position of the actuator element relative to the skin surface is provided as well as at least one actively actuated positioning device for modifying the position of the actuator head and/or the actuator support and a control device for activating the positioning device according to the detected parameter.

6 Claims, 5 Drawing Sheets

HAIR-REMOVING DEVICE

CROSS-REFERENCE TO RELATED APPLICATIONS

This is a continuation of PCT Application No. PCT/EP2003/010829, filed on Sep. 30, 2003, which claims priority to German Patent Application No. 102 46 519.3, filed on Oct. 5, 2002, which is incorporated herein by reference in its entirety.

TECHNICAL FIELD

This invention relates to a hair-removing device, and more particularly to a hair-removing device with a movable actuator head and/or at least one movable actuator support.

BACKGROUND

Movable actuator heads are used, for example, in the form of pivotable shearing heads in electric razors. The mobility of the shearing head is intended to bring about the effect of better contact on the skin surface during shaving, in order in this way to achieve the most optimum possible shaving result.

DE 36 10 736 A1, for instance, discloses an electric shaver with a shearing head system which is pivotably mounted in relation to the housing of the shaver. The shearing head system is set in an oscillating vibrational movement via a drive pin by an electric motor arranged in the housing. During shaving, the shearing head system also performs a passive pivoting movement, i.e., the shearing head system is forced by pressing on the skin surface into a pivoting position which is respectively prescribed by the geometrical situation pertaining. The shearing head system is designed in such a way that, during shaving, as far as possible the entire usable shearing surface constantly comes into contact with the skin surface.

SUMMARY

The hair-removing device has a movable actuator head and/or at least one movable actuator support with at least one actuator element for removing hair on a skin surface. The particular feature of the hair-removing device is that a detecting device for detecting a parameter which relates to the position of the actuator element relative to the skin surface is provided as well as at least one actively actuated positioning device for modifying the position of the actuator head and/or the actuator support and a control device for activating the positioning device according to the detected parameter.

The hair-removing device is design such that optimal skin contact of each actuator element can be constantly achieved. This effect is obtained in particular whenever the hair-removing device has two or more actuator elements which are to be in contact with the skin simultaneously for optimal hair removal. In particular, it is useful in the case of hair-removing devices with a number of actuator elements. In this respect, it is initially immaterial for the applicability of the hair-removing device whether the actuator elements can be positioned individually or in groups or merely all together. If there is altogether only one actuator element, it is generally also possible for the user to establish adequate skin contact even without additional aids. In specific applications, and in particular if the actuator element is movable in a number of planes, use of the hair-removing device may also be used in the case of a hair-removing device with a single actuator element. Further, restrictions existing in the case of passive positioning of the actuator head with respect to the weight and geometry of the actuator head and also with respect to the accessible positioning range are no longer applicable.

A number of actuator heads which are movable independently of one another may be used. An electric drive for the actuator element and/or the positioning device may be arranged in the actuator head. Similarly, it is possible to arrange the electric drive outside the actuator head and to provide a coupling device for coupling the electric drive to the actuator head.

The detecting device may have means for detecting the contact pressure of the actuator element on the skin surface, means for carrying out a capacitive measuring process or means for carrying out an impedance measurement.

In one embodiment, the actuator element is connected to the control device in an electrically conducting manner. Also provided in this embodiment is a housing which is formed at least partially in an electrically conducting manner and is connected to the control device in an electrically conducting manner.

Formation of the detection device by optical means may be used. These can be realized in particular as light barrier system.

A further configuration envisages forming the detection device by at least one displacement, pressure and/or force sensor.

Within the scope of the disclosure there is in particular the possibility of pivotably suspending the actuator head and/or the actuator support.

Alternatively, mounting of the actuator head and/or the actuator support displaceably in at least one plane may be provided.

The hair-removing device may be, for example, an electric razor with at least one shearing foil. The razor may have, in particular, a central cutter which is arranged between two shearing foils. In this case, if the shearing foils and the central cutter are respectively connected to the control device in an electrically conducting manner, information on the position of the shearing foils can be detected with relatively little effort.

Furthermore, it is also possible to form the hair-removing device as a depilating device with at least one plucking unit, since good skin contact is also desirable in this application.

In the case of the method for positioning at least one actuator element of a hair-removing device for removing hair on a skin surface, a parameter which relates to the actual position of the actuator element relative to the skin surface is detected and the actuator element is actively positioned according to the detected parameter. The positioning of the actuator element may take place with the aid of an actuator head and/or with the aid of at least one actuator support, which have at least one actuator element. As a result, virtually any desired positioning movements are possible.

If the detection of the parameter is constantly repeated, allowance can optimally be made for the constantly changing conditions in the handling of the hair-removing device. In another embodiment, the actuator element is positioned in such a way that there is skin contact. To permit certain dynamics, the speed of the positioning can depend on the detected parameter, so that gross positioning errors can be rapidly corrected. Furthermore, the speed of the positioning can be varied during the positioning operation. In order to create a defined starting position in each case, it may be useful to bring the actuator element into a basic position with predeterminable values of the detected parameter. In another embodiment, a current flow which is brought about by contact of the actuator element with the skin surface is detected.

Another development of the method provides that the relative position of the actuator element to the skin surface is detected by optical means. This method is particular stable and practicable in use on wet skin or skin to which care or cleansing products have been applied.

A further development of the method provides that the magnitude of the contact pressure of the actuator element on the skin surface is detected by force, pressure and/or displacement measurement; this is also a particularly reliable method of detection under the conditions described above.

When the hair-removing device is switched off, the actuator element can be brought into a position of rest. In particular, this is of useful whenever the actuator head is thereby brought into a position in which the actuator element is largely protected from external effects.

In the case of the method, at least one further function of the hair-removing device can be controlled according to the detected parameter, so that multiple use of this parameter is possible. In particular, the further function may be the activation of an indicating device, the control of an automatic switching on/off and/or the control of the drive power of an electric drive for the actuator element.

The positioning of the actuator element may take place by a pivoting movement, it also being possible in particular for pivoting movements to be performed with respect to different pivoting axes. The latter is significant when both a pivotable actuator head and at least one pivotable actuator support are present, or if a number of pivotable actuator supports are present.

Alternatively, it may be useful if the positioning of the actuator head or of the actuator support takes place by displacement in at least one plane.

The details of one or more embodiments are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
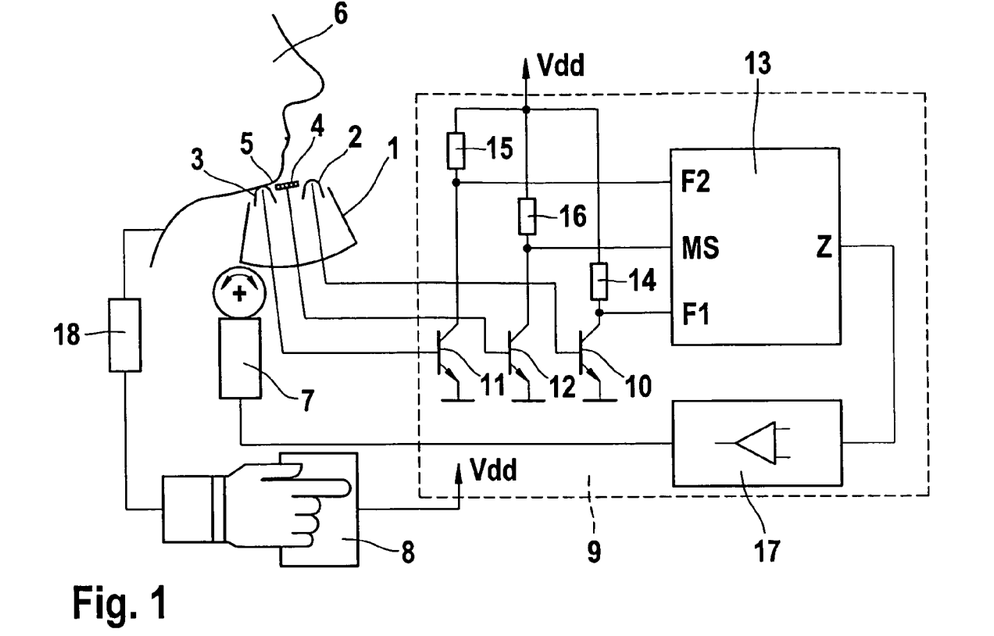
FIG. 1 is a functional diagram for an electric razor according to one embodiment.

FIG. 1 shows a functional diagram for an embodiment of an electric razor. The representation relates to a situation during the action of shaving, individual functional elements of the razor being depicted in a highly schematized form and possible wiring of electronic components that are used for carrying out the positioning method. The embodiment of the razor that is represented has a pivotable shearing head 1, which is mounted pivotably about an axis perpendicular to the plane of the drawing. The shearing head 1 has a first shearing foil 2, a second shearing foil 3 and a central cutter 4, arranged between the shearing foils 2 and 3. In the situation represented, the second shearing foil 3 is in physical contact with a skin surface 5 of a user 6. The shearing head 1 is pivoted by means of a positioning device 7 relative to a housing 8, which the user 6 holds in his hand. The two shearing foils 2 and 3 and also the central cutter 4 are respectively connected to an electronic circuit 9 in an electrically conducting manner, the first shearing foil 2 being connected to the base of a first transistor 10, the second shearing foil 3 being connected to the base of a second transistor 11 and the central cutter 4 being connected to the base of a third transistor 12. The emitters of the transistors 10, 11 and 12 are connected to ground. On the collector side, the first transistor 10 is connected to an input denoted by F1 of a control logic 13 and to a first collector resistor 14. The second transistor 11 is connected to an input denoted by F2 of the control logic 13 and to a second collector resistor 15 and the third transistor 12 is connected to an input denoted by MS of the control logic 13 and to a third collector resistor 16. The control logic 13 has an input denoted by Z, which is connected via a driver stage 17 to the positioning device 7. The collector resistors 14, 15 and 16 are, furthermore, connected to one another and, like the housing 8 which the user 6 holds in his hand, are at an electric potential Vdd. From the housing 8 there is an electrical connection to the second shearing foil 3 via the user 6, affected by a body resistance 18. To make this possible, the housing 8 is formed at least partially in an electrically conducting manner. Depending on the position of the shearing head 1, there may also be corresponding electrical connections to the central cutter 4 and to the first shearing foil 2. The body resistance 18 represents the total effective electrical resistance between the skin surface 5 and the hand of the user 6.

In the case of the embodiment represented in FIG. 1, the functional principle is that the shearing head 1 is in each case pivoted in such a way that the two shearing foils 2 and 3 are in contact with the skin surface 5. Required for this purpose is, on the one hand, information on whether the two shearing foils 2 and 3 are actually in contact with the skin surface 5 and, on the other hand, a mechanism which pivots the shearing head 1 from a position in which at least one of the shearing foils 2 and 3 is not in contact with the skin surface 5 into a position in which both shearing foils 2 and 3 are in contact with the skin surface 5. Information on which of the shearing foils 2 and 3 is in contact with the skin surface 5 is obtained by it being checked with the electronic circuit 9 depicted in FIG. 1 for both shearing foils 2 and 3 whether a current flow is brought about. The current flow respectively runs via the body resistance 18 and can consequently only be formed if the respective shearing foil 2 or 3 is in contact with the skin surface 5. If, for example in a way corresponding to the situation represented in FIG. 1, the second shearing foil 3 is in contact with the skin surface 5 and consequently a current flow is formed through the body resistance 18 to the base of the second transistor 11, the second transistor 11 switches through and connects the input F2 of the control logic 13, which is otherwise at the electric potential Vdd, to ground. The same also applies correspondingly to the first shearing foil 2 when it is in contact with the skin surface 5. Since only very small currents are required for the switching through of the transistors 10, 11,12, the current flow through the body resistance 18 is absolutely safe and imperceptible for the user 6.

The control logic 13 evaluates the signals lying at its inputs and according to them activates the driver stage 17, which in turn controls the positioning device 7 in a corresponding way, so that the shearing head 1 is pivoted in a desired way. The evaluation by the control logic 13 takes place in accordance with a truth table represented as Table 1, which assigns a control command at the output Z of the control logic 13 to each combination of signals at the inputs F1, F2 and MS. For an input of the control logic 13 connected to ground, a "0" respectively appears in the truth table, and, for an input at the electric potential Vdd, a "1" respectively appears, i.e. in the case of a "0" there is skin contact and in the case of a "1" there is no skin contact. The signal at the input MS of the control logic 13 indicates whether the central cutter 4 is in contact with the skin surface 5 and is determined in a way corresponding to the signals at the inputs F1 and F2. Consideration of the signal at the input MS of the control logic 13 is not absolutely necessary, but permits better control of the shearing head 1, since in this way intermediate positions can also be taken into account.

TABLE 1

Truth table

| F1 | F2 | MS | Z |
|----|----|----|---|
| 0 | 0 | 0 | Stop |
| 0 | 0 | 1 | Stop |
| 1 | 1 | 0 | Stop |
| 1 | 1 | 1 | Stop |
| 1 | 0 | 0 | Right-running/slow |
| 1 | 0 | 1 | Right-running/fast |
| 0 | 1 | 0 | Left-running/slow |
| 0 | 1 | 1 | Left-running/fast |

As the truth table shows, the shearing head 1 remains in its position if either both shearing foils 2 and 3 are jointly in contact with the skin surface 5 or neither of the two shearing foils 2 and 3 is in contact with the skin surface 5. It is in each case immaterial here whether or not the central cutter 4 is in contact with the skin surface 5. In a variant, it is also possible to pivot the shearing head 1 slowly into a basic position if either of the two shearing foils 2 and 3 is in contact with the skin surface 5. If only the first shearing foil 2 is not in contact with the skin surface 5, the positioning device 7 is rotated slowly to the right, i.e. in a clockwise direction, in the geometry represented in FIG. 1, and consequently the shearing head 1 is pivoted to the left. If, moreover, the central cutter 4 is also not in contact with the skin surface 5, a more serious positioning error of the shearing head 1 is assumed and the positioning device 7 is therefore rapidly rotated to the right. Conversely, slow rotation to the left of the positioning device 7 takes place if only the second shearing foil 3 is not in contact with the skin surface 5 and fast rotation to the left takes place if, in addition, the central cutter 4 is not in contact with the skin surface 5.

The circuit 9 serves on the one hand as a detection device for detecting information with respect to the position of the two shearing foils 2 and 3 and on the other hand as a control device for activating the positioning device 7 according to the detected information. The detection and the control are in this case repeatedly carried out, in that the test as to whether there is a current flow through the body resistance 18 and the evaluation based on the truth table are constantly repeated. As this happens, the position of the shearing head 1 is modified until the desired skin contact of the two shearing foils 2 and 3 is obtained. The skin contact of the two shearing foils 2 and 3 is consequently established by a kind of closed-loop control circuit. In order to increase the dynamics further and correct the serious positioning error of the shearing head 1 as quickly as possible, it is additionally possible to increase the respective speed during the positioning of the shearing head 1.

If both shearing foils 2 and 3 are in contact with the skin, the difference between the two electrical resistances or the difference between the impedances between a respective shearing foil and the housing 8 can be used for more accurate positioning of the shearing head 1. Such a difference occurs if the skin contact of the two shearing foils is different, i.e. if one shearing foil is pressed more strongly against the skin than the other. Then the shearing head is pivoted until the two resistances or impedances are equal, and consequently both shearing foils are pressed precisely equally strongly against the skin. This is particularly advantageous for optimal shaving.

As an additional function in addition to the pivoting function described above for optimizing skin contact, there may be a standby function, according to which the shearing head 1 is pivoted into a standby position when the razor is switched off. In the standby position, the shearing foils 2 and 3 face the housing 8 and are consequently protected from being damaged by external effects. Similarly, it is possible to form the shearing head 1 in such a way that, by pivoting the shearing head 1, an alternative shearing system instead of the shearing foil system, for example a long-hair cutter or a shearing system for problem zones, is brought into a position for use. Further additional functions may be that a control of indicating elements or automatic switching on of the razor takes place according to whether the housing 8 is touched or whether a component of the shearing head 1 is in skin contact. In particular, it is also possible to reduce the drive power of the razor when none of the components of the shearing head 1 is in skin contact. The latter is particularly appropriate whenever the razor is equipped with a linear motor.

A long-hair cutter function may be realized as a further additional function. In this case, the shearing head can be pivoted by the user pressing a button into a position in which a long-hair cutter known per se that is fitted on the shearing head in a suitable location can be used advantageously. A long-hair cutter of this type has, for example, a fixed comb, which operates together with a blade which is driven in an oscillating manner and has cutting fins.

In the case of the razor, the entire drive system, i.e., both the oscillating drive of individual components of the shearing head 1 and the positioning device 7 for pivoting the shearing head 1, may be integrated in the shearing head 1. This permits any desired pivoting angles of the shearing head 1. Similarly, it is also possible to arrange the respective drives outside the shearing head 1 in the housing 8 of the razor. Such an embodiment is represented in FIG. 2.

Figure 2:
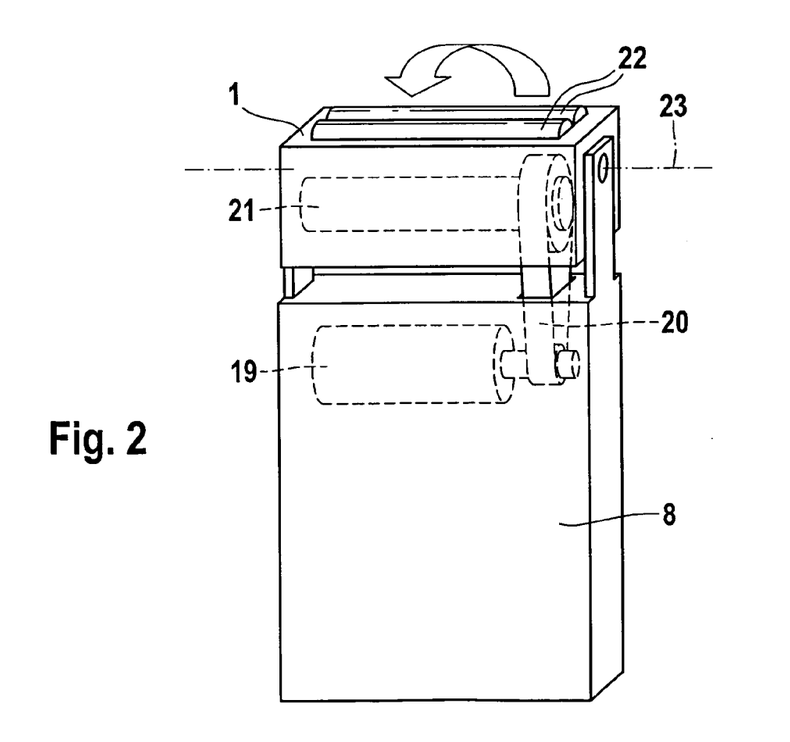
FIG. 2 is a perspective schematic of the electric razor with a drive outside the shearing head.

FIG. 2 shows an embodiment of the razor with a drive outside the shearing head 1 schematically in a perspective representation. In the case of this embodiment, an electric motor 19 is arranged in the housing 8. The movement of the electric motor 19 is transmitted by means of a belt 20 into the region of the shearing head 1. Instead of the belt 20, gear wheels may also be used for example for the transmission of the movement. In the shearing head 1, the belt 20 is coupled to an gear mechanism 21, which carries out an adaptation of the movement transmitted by the belt 20 to the requirements of the shearing head 1 and drives two shearing elements 22, which may comprise for example a shearing foil and a cutter block, which are not represented as such in FIG. 2. Furthermore, the gear mechanism 21 has a coupling element, which is not represented as such and with the aid of which a pivoting movement of the shearing head 1 about the pivoting axis 23 can be triggered. The coupling element is electronically controlled according to the actual position of the shearing head 1, it being possible for the electronic circuit 9 that is represented in FIG. 1 and the control process described there to be used in a corresponding way. In spite of the arrangement of the electric motor 19 outside the shearing head 1, a great pivoting range of +/−180° can be realized with the embodiment of the shearing head 1 that is represented in FIG. 2.

Apart from the applications so far described for razors with a pivotable, but otherwise rigidly formed shearing head 1, the concepts disclosed may be used for razors of different types of construction. Such embodiments are represented in FIGS. 3 and 4.

Figure 3:
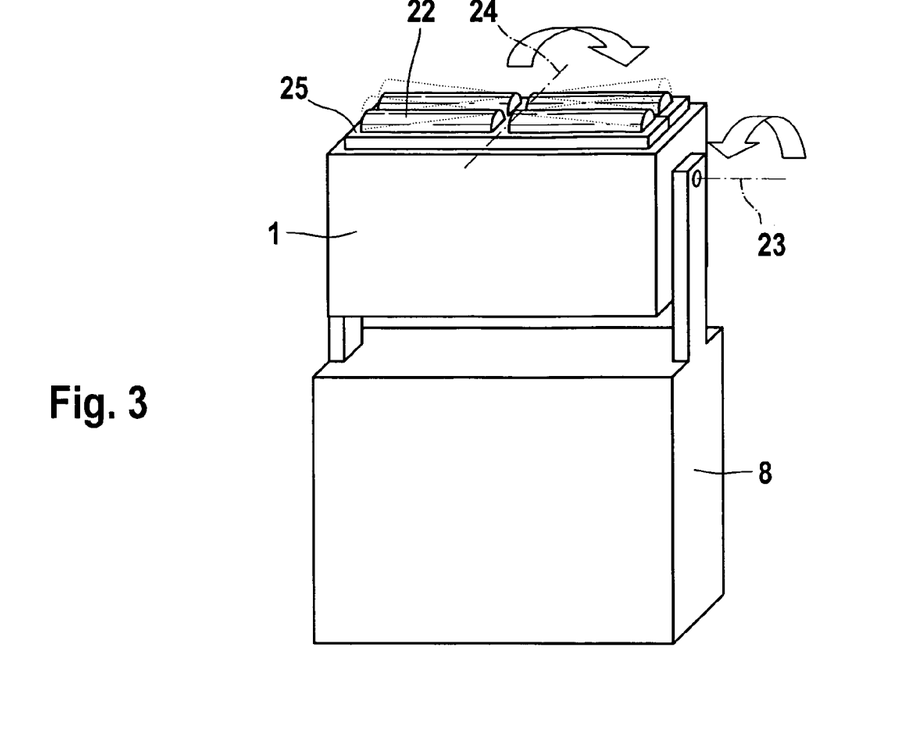
FIG. 3 is an electric razor with multiply movable shearing elements corresponding to FIG. 2.

FIG. 3 shows an embodiment of the electric razor with multiply movable shearing elements 22 in a representation corresponding to FIG. 2. In the case of this embodiment, the shearing head 1 is pivotable about the pivoting axis 23 in a way analogous to the embodiment of FIG. 2. By contrast with FIG. 2, however, this embodiment has a further pivoting axis 24, which is oriented perpendicular to the pivoting axis 23. The additional pivoting possibility is based on the provision of two pivotable supports 25, on which two shearing elements 22 are respectively arranged. Both the pivoting movement about the pivoting axis 23 and the pivoting movement about the further pivoting axis 24 can take place in an active way. Once again it is thereby possible in principle to make use of the electronic circuit 9 and the control process of the embodiment that is represented in FIG. 1, although some adaptations have to be made in the form of additional positioning devices 7 for the independent pivoting of the supports 25 and corresponding inclusion of the additional pivoting movement in the control process. Because of the relatively complex movement sequences, it is recommendable in the case of this embodiment to arrange the drive in the shearing head 1.

Figure 4:
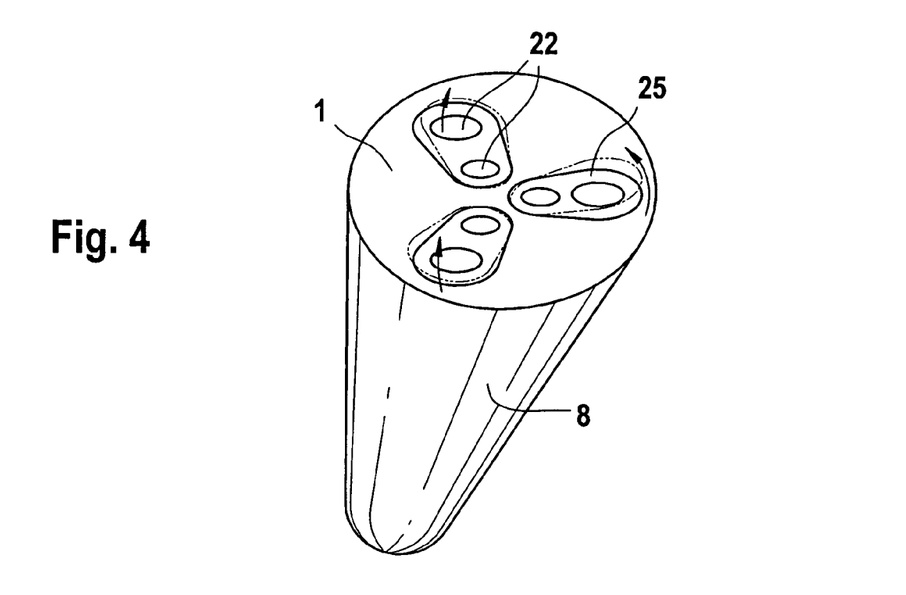
FIG. 4 is an electric razor with a different kind of shearing head system corresponding to FIG. 2.

FIG. 4 shows an embodiment of the razor with a different kind of shearing head system in a representation corresponding to FIG. 2. In the case of this embodiment, the razor does not have a pivotable shearing head 1 but a fixed shearing head 1 with three supports 25, which are movable independently of one another and on each of which two shearing elements 22 are arranged. By contrast with FIG. 3, the supports 25 are not arranged parallel to one another but respectively form an angle of 120° with one another, and are consequently distributed uniformly over the shearing head 1. In spite of the differences in the geometry, the principle of active positioning of the shearing elements 22 is also applied in the case of this embodiment, in that it is determined for each of the three supports 25 to what extent the shearing elements 22 are in skin contact and, according to this, the position of the supports 25 is actively set with the aid of positioning devices 7, which are not visible in the representation of FIG. 4. The positioning of the individual supports 25 takes place in this case independently of one another with the respective aim of establishing the most optimum possible skin contact for the shearing elements 22 arranged on them.

The concepts disclosed may also be used in other devices. One example is depilating devices.

Figure 5:
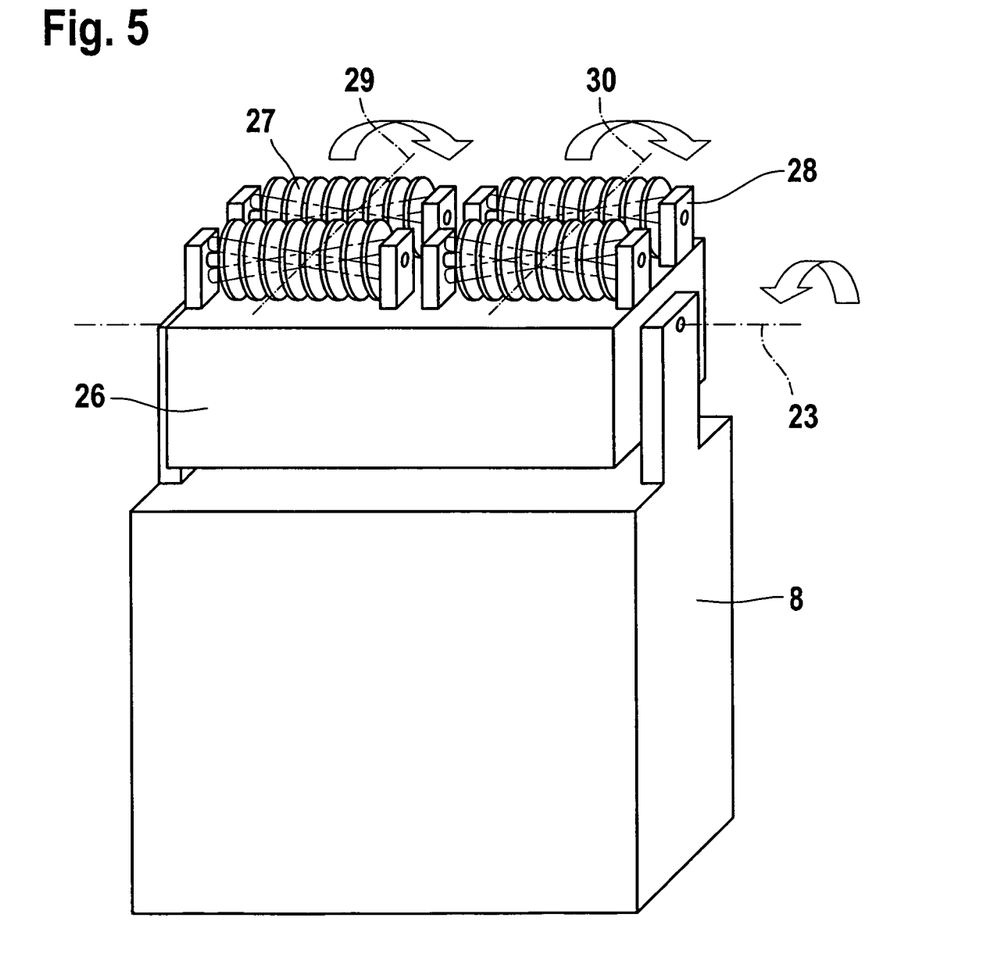
FIG. 5 is a depilating device corresponding to FIG. 2.

FIG. 5 shows an embodiment of a depilating device. This embodiment is very similar with respect to its construction to the razor represented in FIG. 3. For instance, the depilating device has a depilating head 26, which is pivotable relative to the housing 8 about the pivoting axis 23. The depilating head 26 has four rotating plucking units 27, which are respectively fastened in lateral holders 28 in such a way that a pivoting movement is possible. With the geometry represented in FIG. 5, this produces two further pivoting axes 29 and 30, which are arranged parallel to each other and perpendicular to the pivoting axis 23 of the depilating head 26. By analogy with the embodiment of FIG. 3, the entire depilating head 26 and the individual plucking units 27 can be respectively pivoted in such a way that the most optimum possible skin contact is obtained for the individual plucking units 27.

As an alternative to the way described of establishing skin contact by registering the current flow, other procedures for detecting information with respect to the position of the hair-removing elements relative to the skin surface 5 can be used in the case of all the embodiments. For example, force, displacement or pressure sensors may be used, and inductively, capacitively or optically/electronically operating methods may also be used.

Further embodiments of sensor systems for detecting the position of the actuator element relative to the skin surface are represented in FIGS. 6 to 10.

Figure 6:
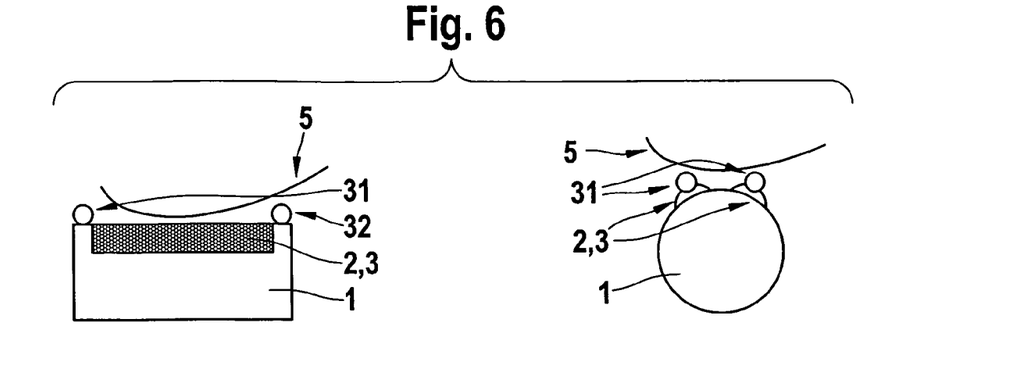
FIGS. 6-10 are further embodiments with different sensors for detection of a measured parameter.

In this respect, FIG. 6 schematically shows in views from the front and the side a shearing head 1, at the lateral boundaries of which on the one hand at least one light transmitter 31 and, lying opposite, at least one light receiver 32 are arranged. In the present example, two light transmitters 31 and two light receivers 32 are respectively arranged, each positioned at the height of the shearing foils 2, 3. This can be seen in particular from the side view in FIG. 6. The light transmitters 31 and the light receivers 32 act as transmission light barriers, which enclose the shaving zone formed by the shearing foils 2, 3. They detect the position of the skin surface 5 relative to the shearing foil 2, 3 and transmit the measuring signals to an assigned signal processing device, which then controls the shearing head control.

Figure 7:
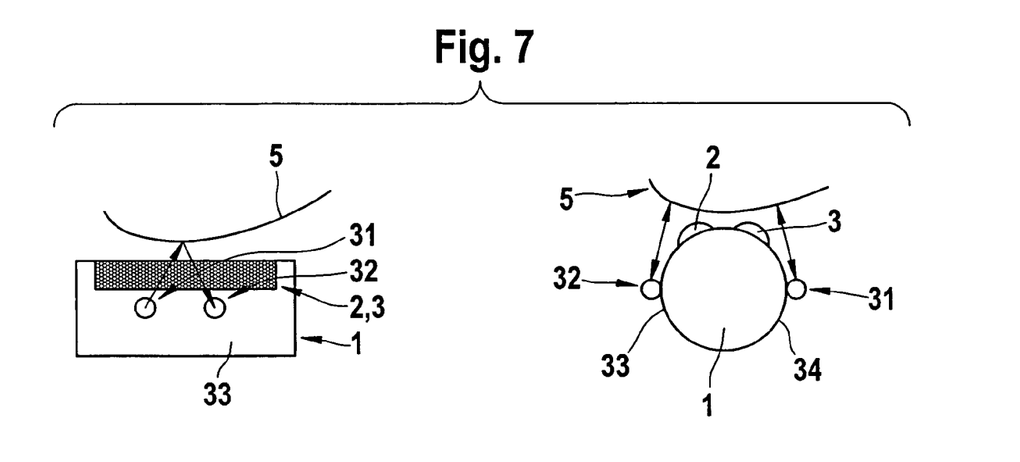

FIG. 7 shows an arrangement of light transmitters 31 and light receivers 32 which act as reflection light barriers. For this purpose, a light transmitter 31 and a light receiver 32 are respectively arranged a lateral distance apart on the front side 33 of the shearing head 1, and the same arrangement is also to be found on the rear side 34.

While in the case of the configuration according to FIG. 6 the amount of light is reduced when the skin surface 5 enters the light barrier defined by the light transmitter 31 and the light receiver 32, to an extent corresponding to the depth by which it enters, it is characteristic in the case of the embodiment according to FIG. 7 that the light emitted by the light transmitters 31 is reflected by the skin surface 5 and is reflected in accordance with the relative position of the skin surface 5 with respect to the shearing head 1 and passed on to the light receivers 32. In correspondence to the distance between the shearing foil 2, 3 and the skin surface 5, the light receivers 32 fitted on the front side 33 and on the rear side 34 are supplied with a corresponding light intensity, which these light receivers then pass on as a corresponding electrical signal to the assigned control device for the adjustment of the shearing head 1. The corresponding path of rays is represented in the two representations according to FIG. 7 by arrows and double-headed arrows (side view).

The light receivers may be formed as photodiodes and the light transmitters may be formed for example as LED or infrared transmitters.

A significant feature of the positional detection between the shearing head 1 and the skin surface 5 by means of light barrier sensor technology is that these sensors not only allow ascertainment of whether there is skin contact but also allow determination of the distance between the shearing head 1 and the skin surface 5 already to be performed before the shearing head 1 is in contact with the skin. As a result, the relative position of the shearing head 1 to the skin surface 5 can already be determined as the shearing head 1 approaches the skin surface 5, and the shearing head 1 can be correspondingly positioned. As soon as the shearing foils 2, 3 are in contact with the skin, the depth to which the respective shearing foils 2, 3 enter the skin surface 5 can be detected by the sensor technology, whereby the corresponding positioning mechanism can be controlled in such a way that both shearing foils 2, 3 enter to the same depth or produce the same skin contact pressure.

Figure 8:
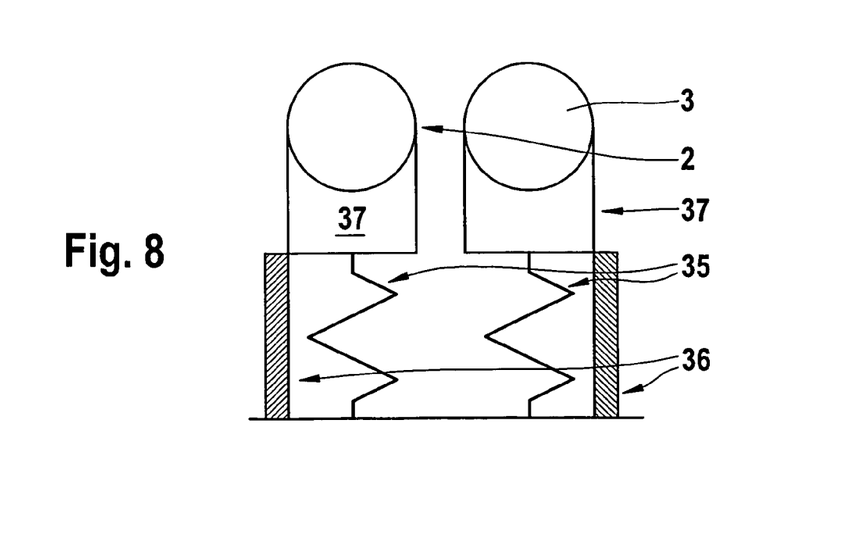
Figure 9:
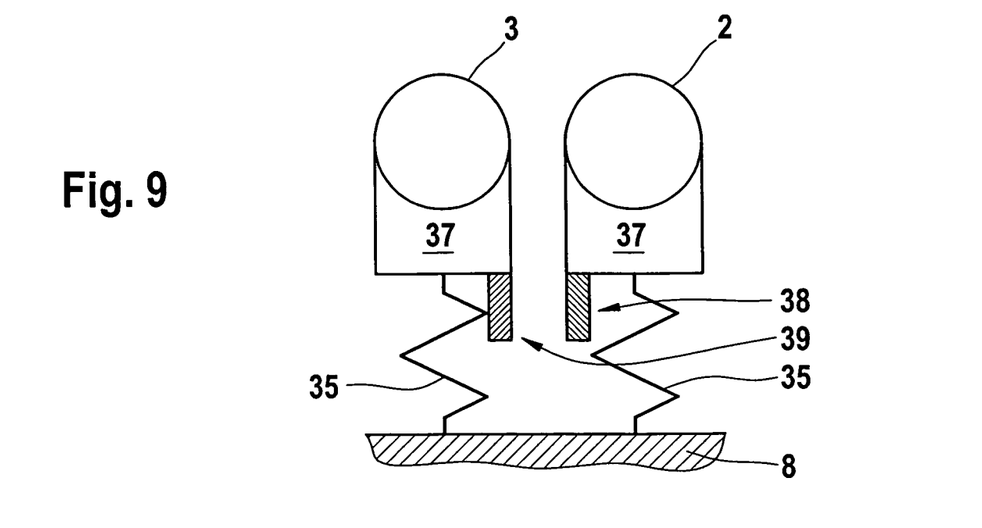
Figure 10:
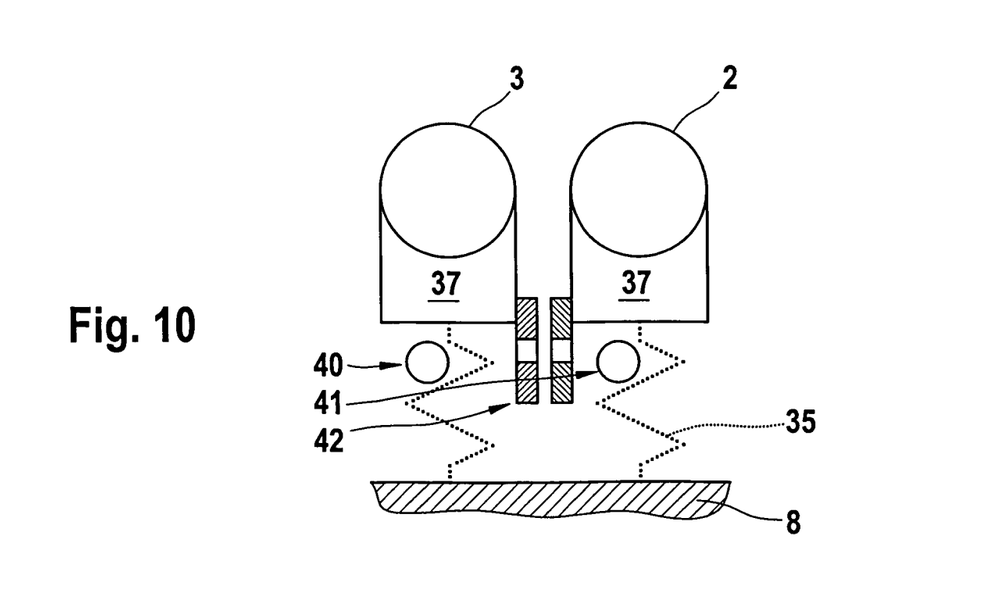

FIGS. 8, 9 and 10 respectively show embodiments in which displacement, pressure or force sensors of various kinds are used for sensing the contact pressure conditions between the actuator head and the skin surface. Additionally represented in these figures are shearing systems 37 which not only allow themselves to be adapted to the required position by pivoting but are particularly suitable for being brought into the required position by corresponding linear displacement. It goes without saying that a combination of linear displacement and pivoting can also be performed. The actuators allowing this linear displacement to be performed are not represented in the drawing for the sake of overall clarity.

FIG. 8 shows two shearing systems 37 with shearing foils 2, 3, which are pretensioned in the direction of the skin surface by means of at least one spring 35 in each case. In addition to the springs, the shearing systems are also supported on the housing by means of force, pressure and/or displacement sensors 36. The measured parameter determined by the displacement, pressure or force sensor and converted into an electrical signal then serves for controlling the assigned positioning drive.

FIG. 9 shows a force or displacement measuring device, which always measures the relative position between the two shearing systems. This differential measurement may also be used in addition to an absolute measurement. The construction that is schematically represented by the drawing in the figure provides for this purpose that the two shearing systems 37 are supported on the housing by means of springs 35 and, in a way similar to in the embodiment according to FIG. 8, are mounted in a longitudinally displaceable manner. In this case, one of the two shearing systems bears a first sensor element 38, while the other shearing system is provided with a second sensor element 39. These sensor elements 38, 39 are capable of detecting their relative movement and/or their relative distance from each other. For example, the first sensor element 38 may be formed as an LED or other light source, while the associated second sensor element 39 is realized by a photosensor. The first sensor element 38 may, however, also be a magnet, to which a Hall sensor is assigned as a second sensor element 39. As a further example, the first sensor element 38 may also be a metal element, the position of which can be detected by a coil through which current flows, the form in which the second sensor element 39 is provided.

Finally, FIG. 10 also shows a measuring arrangement for positional determination in which both the relative position and the absolute position of individual shearing systems 37 can be detected. Provided fixedly on the housing for this purpose is a transmitter element 40, which corresponds to a further fixedly arranged receiver element 41. The two displaceably mounted shearing systems 37 respectively bear an intermediate element for influencing the signal transferred from transmitter element 40 to the receiver element 41. Depending on the position in which each one of the two shearing systems 37 is displaced with respect to a normal position, the signal of the transmitter element is received in a correspondingly influenced manner by the receiver element 41. The receiver element 41 then generates a corresponding electrical signal, which is then passed on to the associated evaluation device for controlling the positioning mechanism. A wide variety of physical effects can be used for this purpose. For example, the transmitting element 40 may be formed as a light source which radiates rays of light to the receiver element 41 formed as a photosensor. The intermediate elements 42 may be configured as suitable optical diaphragms or shutters, which correspondingly influence the path of rays between the elements 40 and 41. Further conceivable configurations of this measuring system may be realized by a magnet as the transmitting element 40 with an assigned Hall sensor as the receiver element 41. It is also possible to form the receiver element 41 as an electrical coil to which a corresponding metal core is assigned.

A number of embodiments of the invention have been described. Nevertheless, it will be understood that various modifications may be made without departing from the spirit and scope of the invention.

What is claimed is:

1. An electric razor for removing hair from a skin surface, comprising:
   a movable actuator head, wherein the movable actuator head defines a first pivoting axis about which the head may pivot;
   a movable actuator element, moveably attached to said movable actuator head;
   a pivotable support, wherein the pivotable support defines a second pivoting axis about which the actuator element may pivot;
   a detecting device for detecting a parameter which relates to the position of the actuator element relative to the skin surface;
   an actively actuated positioning device for modifying the position of the movable actuator head the movable actuator element, or the movable actuator head and the movable actuator element; and a control device for activating the positioning device according to the detected parameter;
   wherein said actuator head is a pivotable shearing head said shearing head connected to said movable actuator element, said movable actuator element comprising, a first shearing foil, a second shearing foil and a central cutter arranged between the shearing foils; said electric razor further comprising a housing, which a user holds in the hand; and wherein said shearing foils and the central cutter are respectively connected to said detecting device, which comprises an electronic circuit, in an electrically conducting manner, the first shearing foil being connected to a first transistor, the second shearing foil being connected to a second transitor and the central cutter being connected to a third transitor, the emitters of the transistors being connected to ground; the firs transistor being connected to an input of a control logic and to a firs collector resistor; the second transistor being connected to an input of the control logic and to a second collector resistor and the third transistor being connected to an input of the control logic and to a third collector resistor; said control logic having an input which is connected via a driver stage to said positioning device; and wherein said collector resistors are also connected to one another and are at an electric potential; wherein the housing is at least partially electrically conducting and comprises an electrical connection to the second shearing foil via the user.

2. The device of claim 1 wherein the actuator head is pivotably suspended.

3. The device of claim 1 wherein the actuator head is displaceable in at least one plane.

4. The device of claim 3 further comprising a movable actuator support attached to the actuator head, wherein the actuator support is displaceable in at least one plane.

5. The device of claim 1 further comprising a long-hair cutter arranged on the actuator head, the long-hair cutter comprising a comb and a blade.

6. The device of claim 1 further comprising at least one plucking unit attached to the actuator head.

\* \* \* \* \*

UNITED STATES PATENT AND TRADEMARK OFFICE
CERTIFICATE OF CORRECTION

PATENT NO. : 8,627,573 B2  
APPLICATION NO. : 11/099018  
DATED : January 14, 2014  
INVENTOR(S) : Bernhard Kraus et al.

It is certified that error appears in the above-identified patent and that said Letters Patent is hereby corrected as shown below:

In the Claims:

Column 10

Line 27, add a --,-- after the words "movable actuator head"

Line 45, delete "firs" and insert --first--

Line 47, delete "firs" and insert --first--

Signed and Sealed this
Eleventh Day of March, 2014

Michelle K. Lee
*Deputy Director of the United States Patent and Trademark Office*